US007170974B2

(12) United States Patent
Groh et al.

(10) Patent No.: US 7,170,974 B2
(45) Date of Patent: Jan. 30, 2007

(54) X-RAY DEVICE

(76) Inventors: Burkhard Groh, 1741 N. Wolcott Ave., Chicago, IL (US) 60622; Volker Heer, In der Hasenleite 25, 96163 Gundelsheim (DE); Mathias Hömig, Gerhart-Hauptmann-Str. 1, 91058 Erlangen (DE); Bernhard Sandkamp, Schwabachanlage 1, 91054 Erlangen (DE)

(*) Notice: Subject to any disclaimer, the term of this patent is extended or adjusted under 35 U.S.C. 154(b) by 112 days.

(21) Appl. No.: 10/992,174

(22) Filed: Nov. 18, 2004

(65) Prior Publication Data

US 2005/0169426 A1 Aug. 4, 2005

(30) Foreign Application Priority Data

Nov. 24, 2003 (DE) ................................ 103 54 899

(51) Int. Cl.
*H05G 1/64* (2006.01)

(52) U.S. Cl. ........................ 378/98.8; 378/62; 378/197

(58) Field of Classification Search .................. 378/19, 378/62, 98.8, 101, 108, 109, 197; 250/370.09, 250/370.11

See application file for complete search history.

(56) References Cited

U.S. PATENT DOCUMENTS 5,355,309 A * 10/1994 Eberhard et al. ............. 378/15
6,222,906 B1 * 4/2001 Sakaguchi et al. ......... 378/98.8
6,477,230 B1 * 11/2002 Fuchs et al. .................. 378/98
6,516,046 B1 2/2003 Fröhlich et al.
6,618,468 B1 * 9/2003 Klotz et al. .............. 378/98.12
6,792,070 B1 * 9/2004 Sakaida ........................ 378/62
6,928,142 B1 * 8/2005 Shao et al. ................... 378/63

FOREIGN PATENT DOCUMENTS

DE 199 53 177 A1 6/2001

* cited by examiner

*Primary Examiner*—Edward J. Glick
*Assistant Examiner*—Jurie Yun

(57) ABSTRACT

An X-ray device (1) is provided including an X-ray source (8) and a first X-ray detector (9,100) for producing a first X-ray image data set of an examination object (P). A second X-ray detector (20) is provided for producing a second X-ray image data set of examination object (P) where the second X-ray detector (20) has a smaller detector surface (23) than the first X-ray detector (9,100). The second X-ray detector (20) may produce an X-ray image associated with the second X-ray image data set that has a higher local resolution than the X-ray image (12) associated with the first X-ray image data set. The second X-ray detector (20) may be movably connected with the first X-ray detector (9,100) so the second X-ray detector (20) maybe articulated upstream of the first X-ray detector (9,100).

19 Claims, 5 Drawing Sheets

X-RAY DEVICE

CROSS REFERENCE TO RELATED APPLICATIONS

This application claims priority to the German application No. 10354899.8, filed Nov. 24, 2003 which is incorporated by reference herein in its entirety.

FIELD OF INVENTION

The invention relates to an X-ray device and a method for producing an X-ray image data set

BACKGROUND OF INVENTION

An X-ray device essentially comprises an X-ray source and an X-ray detector. An X-ray beam is emitted from the X-ray source during an X-ray recording, said X-ray beam being attenuated as it passes through an examination object, a patient for instance, and striking the X-ray detector. By means of signal processing, the X-ray detector, which comprises an X-ray image amplifier or a flat panel detector with a downstream electronic readout unit, converts the X-ray intensity distribution striking the detector surface of the X-ray detector to an X-ray image data set, the associated X-ray image of which can in turn be displayed with a display device.

SUMMARY OF INVENTION

It has hitherto been necessary, particularly in angiography and here specifically in neurology, to display subareas of the X-ray image in enlarged form, in order to display relatively small structures, e.g. small vessels or stent structures for instance. Since the local resolution of the X-ray image recorded with the X-ray detector is limited, the local resolution of the enlarged subarea can be unsatisfactory. A higher resolution X-ray detector is not used for reasons of cost.

An object of the invention is thus to design an X-ray device of the type mentioned at the beginning such that it can be used to produce an X-ray image, which displays a subarea of a previously recorded X-ray image with a higher local resolution. The object of the invention is also to specify a method which produces an X-ray image which displays a subarea of a previously recorded X-ray image with a higher resolution.

The object of the invention is achieved by an X-ray device with an X-ray source and a first X-ray detector for generating a first X-ray image data set of an examination object, characterized in that the X-ray device has a second X-ray detector for generating a second X-ray image data set of an examination object, whereby the second X-ray detector has a smaller detector surface than the first X-ray detector and is designed such that the X-ray image associated with second X-ray image data set has a higher local resolution than the X-ray image associated with the first X-ray image data set.

The fundamental idea behind the X-ray device according to the invention is additionally to provide the X-ray device with a second smaller X-ray detector having a particularly square, rectangular or circular detector surface of between 15 $cm^2$ and 100 $cm^2$ according to one embodiment of the invention and a small height of less than 3 cm. The second X-ray image detector enables the production of X-ray images with a higher local resolution. Provision is made in particular to produce a further X-ray recording of the examination object having a higher local resolution for a subarea of an X-ray recording, which was recorded using the first X-ray detector. The second X-ray detector can thereby be operated in particular in fluoroscopy mode or recording mode.

According to a variant of the invention a flat plane detector, the detector elements of which have edge lengths in particular of 20 μm to 80 μm, is used as the second X-ray detector in order to achieve an X-ray image with the highest possible local resolution using the second X-ray detector.

A flat panel detector is an X-ray detector, having essentially an X-ray receptor, a high-resolution sensor and a low noise and high-performance electronic readout unit. The X-ray receptor has a scintillator for instance, comprising in particular cesium iodide or directly converting materials, such as cadmium telluride for example. The high-resolution sensor is a CCD chip, a CMOS chip or an aSi flat panel detector for instance.

The second X-ray detector is arranged on a mechanical holding device of the X-ray device according to one embodiment of the invention, so that said second X-ray detector can be moved, if necessary, with the mechanical holding device into the X-ray path emitted from the X-ray source. If the second X-ray detector is not required, it can be parked in a park position, adjacent to or behind the first X-ray detector for example. In particular the second X-ray detector for recording the second X-ray image data set can be positioned directly in front of the first X-ray detector.

Components required to obtain the first X-ray image data set, such as the image processing software provided for the first X-ray image data set, can be used to produce the X-ray image associated with the second X-ray image data set or for signal processing of the second X-ray image data set.

According to a variant of the invention, the X-ray dose controller associated with the first X-ray detector can be used to control the dose of the second X-ray detector, as the second X-ray detector is smaller than the first X-ray detector and thus completely absorbs the incident X-rays, in particular when positioned directly in front of the first X-ray detector, so that the first X-ray detector can similarly absorb incident X-rays.

It is generally not necessary to reduce X-ray radiation scatter due to the relatively small detector surface of the second X-ray detector. A-high-resolution radiation scatter raster can be integrated, if it is necessary to reduce the X-ray radiation scatter.

A so-called organ program can be provided to operate the second X-ray detector, said organ program determining the X-ray dose to be applied, the required image frequency or parameters of digital image processing. Selection of the resolution stage, with which several detector elements of the second X-ray detector are combined in a detector element group, can also be provided for. The X-ray device according to the invention can comprise a further selection, with which the second X-ray detector is positioned geometrically in relation to the first X-ray detector. For this the inventive X-ray device according to a preferred exemplary embodiment of the invention comprises a display device for displaying the X-ray image associated with the first X-ray image data set, means for selecting an area of the X-ray image associated with the first X-ray image data set and displayed using the display device and means for positioning the second X-ray detector, with which the second X-ray detector can be positioned in the X-ray path emitted from the X-ray source such that the X-ray image associated with the second X-ray image data set includes the selected area.

The display device is thereby preferably a touch screen, so that the means for selecting the area are provided by touching the area of the X-ray image displayed using the touch screen and associated with the first X-ray image data set. The means for selecting the area can also comprise a marker which can be superimposed on the display device and moved by means of a joystick for example.

The object of the invention is also achieved by a method for producing an X-ray image data set comprising the following method steps;

Producing a first X-ray image data set of an examination object by means of a first X-ray detector of an X-ray device comprising an X-ray source and the first X-ray detector.

Displaying the X-ray image associated with the first X-ray image data set using a display device Selecting an area in the X-ray image associated with the first X-ray image data set Automatic positioning of a second X-ray detector in the beam path emitted from the X-ray source such that the second X-ray detector produces a second X-ray image data set of the examination object, the associated X-ray image of which has a higher local resolution than the X-ray image associated with the first X-ray image data set and maps the selected area, and Producing the second X-ray image data set According to the invention the X-ray image of the examination object associated with the first X-ray image data set is produced and displayed on a display device using the X-ray device comprising the first X-ray detector and the X-ray source. To display a subarea of the displayed X-ray image with a higher local resolution, in particular an enlarged form, this area is initially selected. If the display device is a touch screen for example, the area can be selected in a simple manner by correspondingly touching the touch screen. With a conventional display device, the area can be selected with a marker superimposed on the display device, a cursor for instance, whereby the marker is moved using a joystick or a mouse for example and the actual area is selected by clicking.

After the area has been selected, the second X-ray detector with which X-ray images can be recorded, which have a higher local resolution than the X-ray images recorded using the first X-ray detector, is positioned automatically in the beam path emitted from the X-ray source such that the second X-ray image data set, which maps the selected area, can be produced. For this purpose, according to a preferred variant of the method according to the invention for instance a data processing device of the X-ray device determines the image coordinates associated with the selected area and positions the second X-ray detector directly in front of the first X-ray image detector and at the point corresponding to the determined coordinates.

An X-ray recording of the examination object is then made using the second X-ray detector, i.e. the second X-ray image data set is produced. The X-ray image associated with the second X-ray image data set then displays the selected area of the X-ray image associated with the first X-ray image data with higher local resolution.

In particular a relatively small X-ray detector, which according to an embodiment of the invention, has a particularly square, rectangular, or circular detector surface of between 15 $cm^2$ and 100 $cm^2$, is used as the second X-ray detector. The second X-ray detector can be operated in particular in fluoroscopy mode or even in recording mode.

According to a variant of the invention a flat panel detector, the detector elements of which have edge lengths in particular of 20 μm to 80 μm, is used as a second X-ray detector in order to achieve an X-ray image with the highest possible local resolution using the second X-ray detector.

A flat panel detector is an X-ray detector, having essentially an X-ray receptor, a high-resolution sensor and a low noise and high-performance electronic readout unit. The X-ray receptor has a scintillator for instance, comprising in particular cesium iodide or directly converting materials, such as cadmium telluride for example. The high-resolution sensor is a CCD chip, a CMOS chip or an aSi flat panel detector for instance.

BRIEF DESCRIPTION OF THE DRAWINGS

Exemplary embodiments are shown by way of an example in the schematic drawings, in which.

DETAILED DESCRIPTION OF INVENTION

Figure 1:
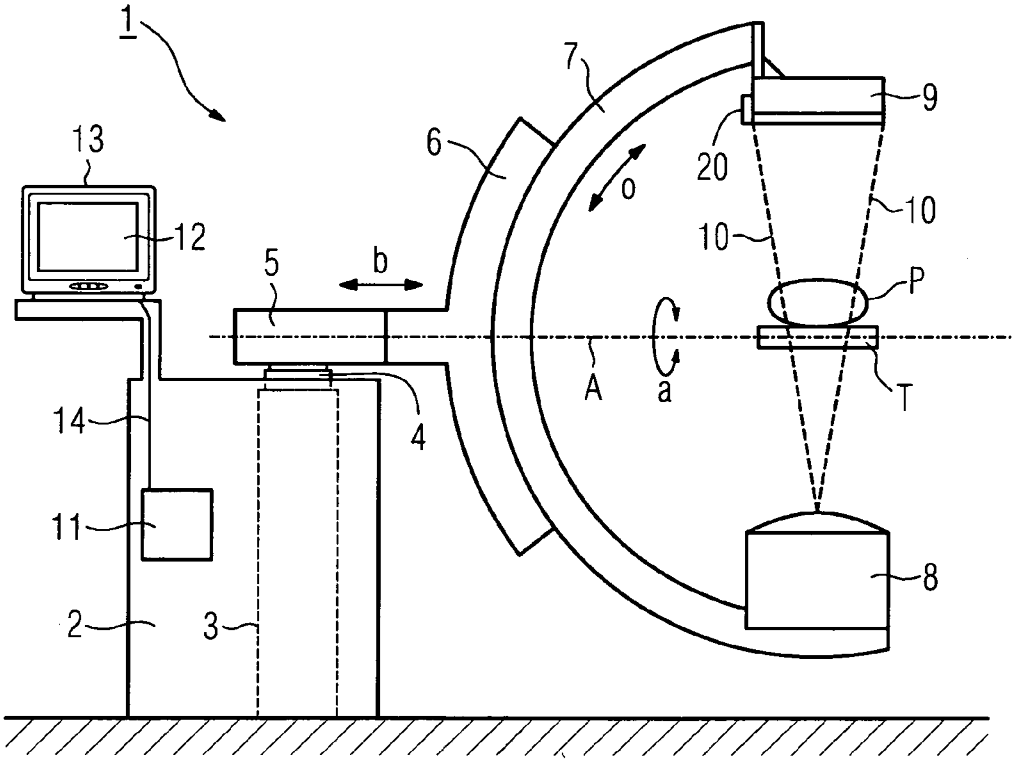
FIG. 1 shows an X-ray device displayed partially as a block diagram having two X-ray detectors

FIG. 1 shows an X-ray device according to the invention in the form of a C-arm X-ray device 1 at least partially as a block diagram. The C-arm X-ray device 1 has a housing 2, within which a lifting device 3 with a column 4, shown only schematically in FIG. 1, is arranged. A holding section 5 is arranged on the column 4, on which a bearing section 6 in turn is arranged to support a carrier device configured as a C-arm 7. The C-arm 7 comprises an X-ray source 8 and an X-ray detector, which is a first flat panel detector 9 in the case of the present exemplary embodiment. The X-ray source 8 and the first flat panel detector 9 are arranged on the C-arm 7 relative to one another such that an X-ray beam 10, the marginal rays of which are shown in FIG. 1 by means of a dashed line, emitted from the X-ray source 8 strikes the first flat panel detector 9.

The bearing section 6 is supported on the holding section 5 such that it can be rotated in a manner known per se about a common axis A of the holding section 5 and of the bearing section 6 (see double arrow a, angulation) and can be moved in the direction of the axis A (see double arrow b). The C-arm 7 is supported on the bearing section 6 along its periphery so that it can be moved in the direction of the double arrow o, relative to the bearing section 6 (orbital movement). The lifting device 3 enables the C-arm 7, which is connected to the column 4 of the lifting device 3 by means of the bearing section 6 and the holding section 5, to be adjusted vertically relative to the housing 2 of the C-arm X-ray device 1.

The C-arm X-ray device 1 further comprises the most transparent table T possible for X-rays, on which a patient P lies during an X-ray recording. The supports of the table T are not shown in FIG. 1 for purposes of clarity. During an X-ray recording of an area of interest of the patient P, the X-ray beam 10 emitted from the X-ray source 8 is attenuated as it passes through the patient P and strikes the first flat panel detector 9 as an X-ray intensity distribution. The first flat panel detector 9, which comprises a generally known downstream electronic readout unit, is in turn connected to a computer 11 by means of electric cables (not shown for purposes of clarity in FIG. 1). A signal processing program operates on the computer 11, which converts the output signals of the first flat panel detector 9 with a downstream electronic readout unit, which are associated with the X-ray intensity distribution striking the detector surface of the flat panel detector 9, to an X-ray image data set, the associated X-ray image 12 of which can in turn be displayed using a display device, which in the present exemplary embodiment is a touch screen 13. The touch screen 13 is connected to the computer 11 via an electric cable 14.

Furthermore the first flat panel detector 9 comprises a dose controller, not specified explicitly in FIG. 1, but known to the person skilled in the art.

The C-arm X-ray device 1 further comprises a second flat panel detector 20 which, in the case of the present exemplary embodiment is fixed to the first flat panel detector 9 by means of a holding device 21.

Detailed views of the two flat panel detectors 9 and 20 are shown in FIGS. 2 to 6.

The second flat panel detector 20 is provided in particular to display subareas of an X-ray recording produced using a first flat panel detector 9, such as the X-ray image 12, with higher local resolution. In the case of the present exemplary embodiment, the detector elements 22 of the second flat panel detector 20 have edge lengths of 50 μm. Furthermore, the detector surface 23 of the second flat panel detector 20 is smaller than the detector surface 9*a* of the first flat panel detector 9. The detector surface 23 of the second flat panel detector 20 is 50 $cm^2$ in the case of the present exemplary embodiment.

The second flat panel detector 20 is fixed to a holding device 21 which is shown in more detail in FIGS. 2 to 6. In the case of the present exemplary embodiment, the holding device 21 comprises a guide rail 26, on which the second flat panel detector 20 is arranged so that it can be folded back by means of an electric motor 29 and can be moved along the double arrow c shown in FIG. 5 directly in front of the detector surface 9*a* of the first flat panel detector 9 by means of an electric motor 27. The electric motors 27 and 29 are connected to the computer 11 of the C-arm X-ray device 1 by means of electric cables (not shown) and can be controlled using an input element of the computer 11, for instance a keyboard (not shown for purposes of clarity).

The guide rail 26 of the holding device 21 is in turn arranged on two guide rails 25 and 25*a* of the holding device 21, and can be moved by means of an electric motor 28 along a double arrow d relative to the detector surface 9*a* of the first flat panel detector 9. The electric motor 28 is also connected to a computer 11 by means of electric cables (not shown) and can be controlled thereby.

Figure 2:
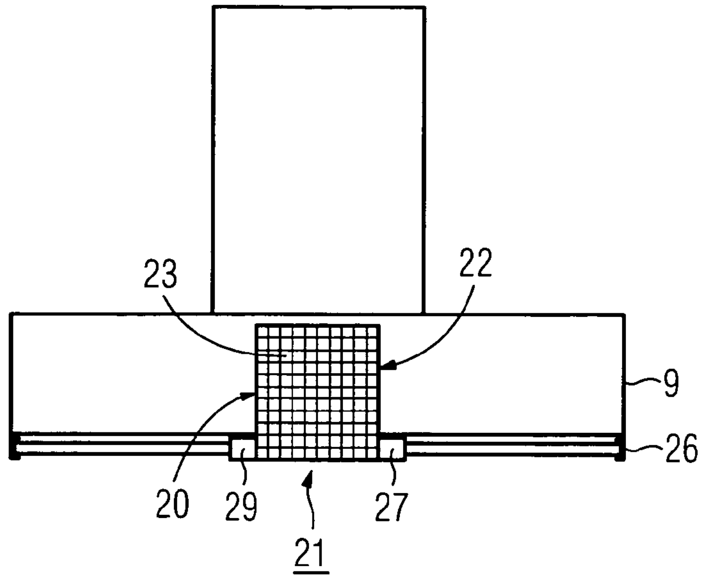
FIGS. 2 to 6 show partial views of the X-ray detectors shown in FIG. 1
Figure 3:
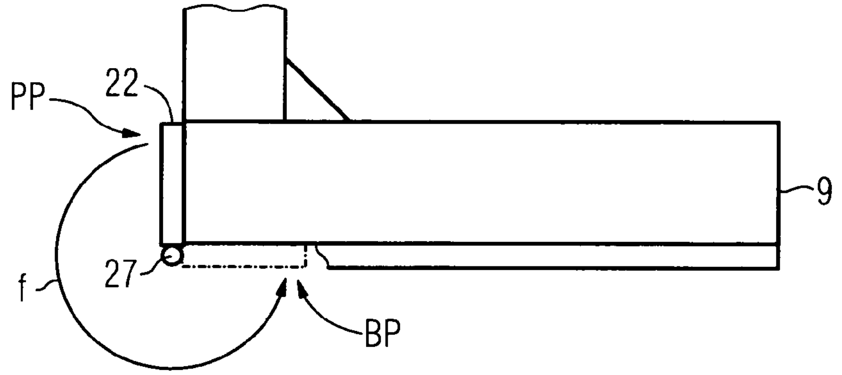
Figure 4:
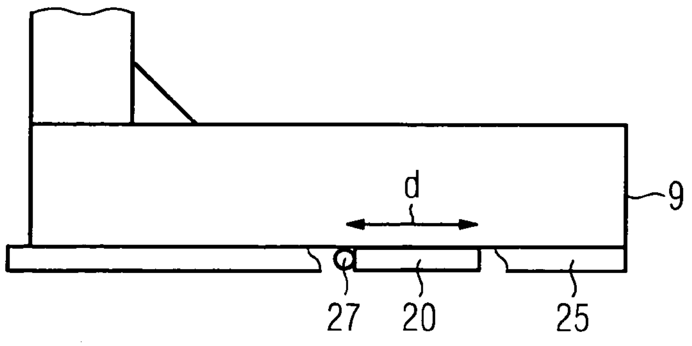
Figure 5:
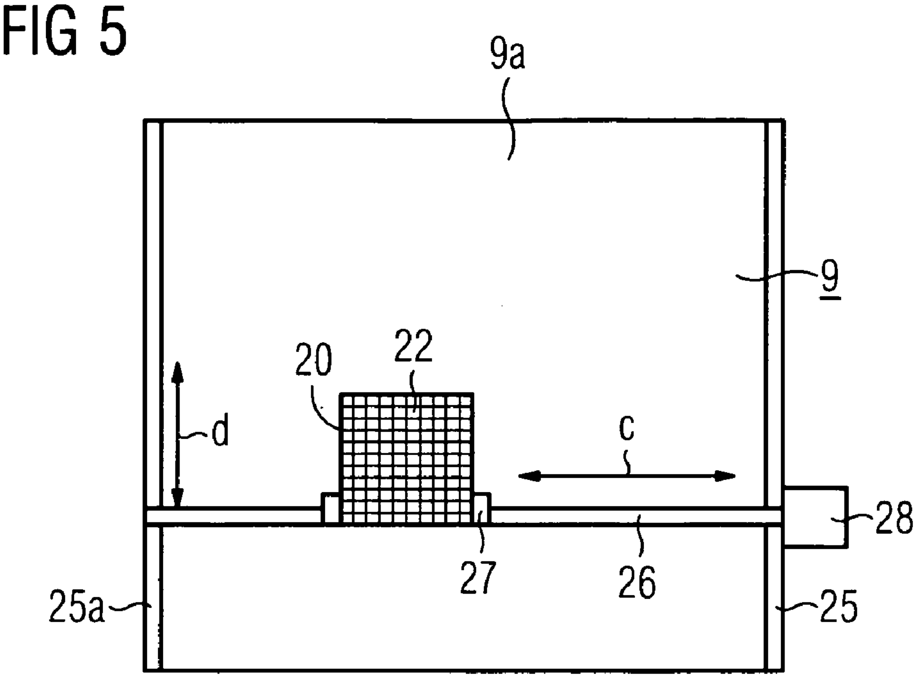
Figure 6:
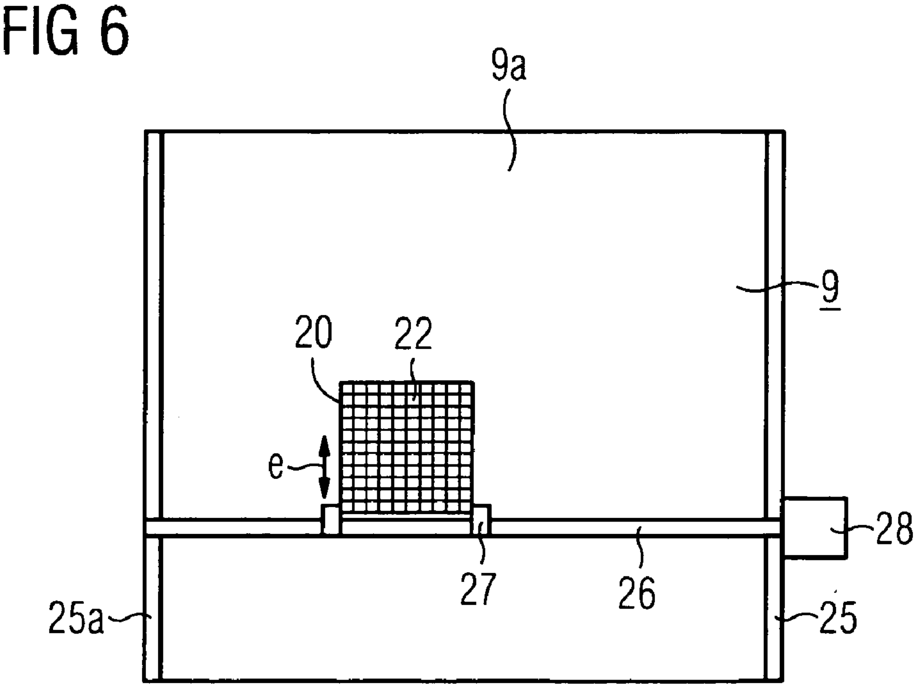

If the second flat panel detector 20 is not required, it is folded up behind the first flat panel detector 9 in a 'park position' PP, as shown in FIGS. 2 and 3. If the second flat panel detector 20 is required for an X-ray recording, in the case of the present exemplary embodiment it can be activated in a first operating mode by means of the above mentioned keyboard, by for example pressing one of the keys of the keyboard associated with the first operating mode. After activating the first operating mode, the computer 11 activates the electric motor 29 such that the second flat panel detector 20 folds over from its park position PP along the arrow f into its operating position BP, as shown in FIG. 3. In the case of the present exemplary embodiment, the second flat panel detector 20 is then moved into the required position for the X-ray recording by means of the arrow keys on the above-mentioned keyboard. For this the computer 11 activates the two electric motors 27 and 28 accordingly. If the second flat panel detector 20 is in the required position for the X-ray recording, in the case of the present exemplary embodiment the second flat panel detector is moved out using a linear motor (not shown) connected to the computer 11 relative to the arrow e shown in FIG. 6.

To simplify the task of locating the required position of the second flat panel detector 20, the C-arm X-ray device 1 can be operated in fluoroscopy mode for the first operating mode. Furthermore in the case of the present exemplary embodiment provision is made for the dose controller of the first flat panel detector 9 also to be used to control the dose of the second flat panel detector 20. The signal processing operating on the computer 11 is also used for the signal processing of the output signals of the second flat panel detector 20, so that the computer 11 can calculate an X-ray image data set from these output signals, the associated X-ray image of which can be observed with the touch screen 13.

In the case of the present exemplary embodiment, the second flat panel detector 20 can still be operated in a second operating mode. If the second operating mode is activated, an operator of the C-arm X-ray device 1 can select a subarea of an X-ray image produced using the first flat panel detector 9 and displayed with the touch screen 13, the X-ray image 12 for instance, in the case of the present exemplary embodiment by touching the required subarea on the touch screen 13. The touch screen 13 then transmits an electrical signal associated with the touched position on the touch screen 13 via an electric cable 14 to the computer 11, which is in turn configured such that it calculates the image coordinates of the touched position in the X-ray image 12 displayed based on this electrical signal. If the patient P has not moved or has only moved slightly since the X-ray recording associated with the X-ray image 12 and if the C-arm 7 remains similarly unchanged relative to the patient P or the table T, a direct association results between the determined image coordinates and the position associated with these image coordinates at the detector surface 9*a* of the first flat panel detector 9. It is thus known, to which position the second flat panel detector 20 must be moved in respect of the detector surface 9*a* of the first flat panel detector 9, so that an X-ray image of the selected subarea can be produced using the second flat panel detector 20. To guide the second flat panel detector 20 to said position, the computer 11 now activates the electric motors 27 and 28 in a suitable manner.

FIGS. 7 to 10 show an alternative embodiment of the support 21 of the second flat image detector 20. The alternative support is assigned the reference character 70.

Figure 7:
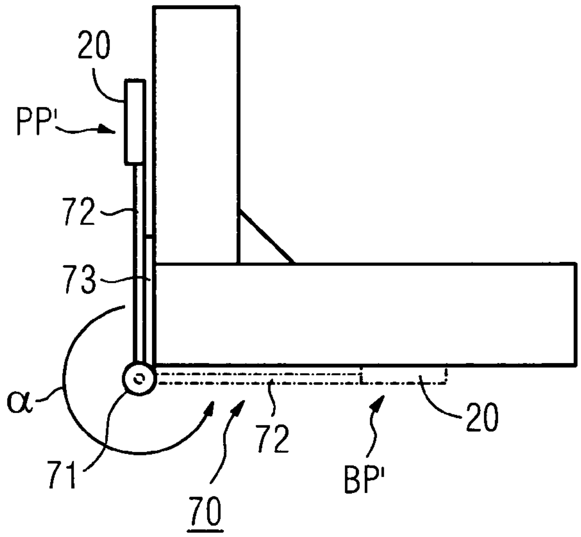
FIGS. 7 to 13 show alternative models of the X-ray detectors shown in FIG. 1.

The support 70 comprises a holding section 72, supported so that it can be pivoted using an electric motor 71, on which the flat panel detector 20 is arranged. The electric motor 71 is connected to the computer 11 by means of the electric cables (not shown in the Figures) and is activated by said computer. If the flat panel detector 20 is not required, the holding section 72 is folded up behind the first flat panel detector 9 in a 'park position', as shown in FIG. 7. If the flat panel detector 20 is required for an X-ray recording, the electric motor 71 is activated by the computer 11 and folds the holding section 72 along the arrow α into its operating position BP'.

Figure 8:
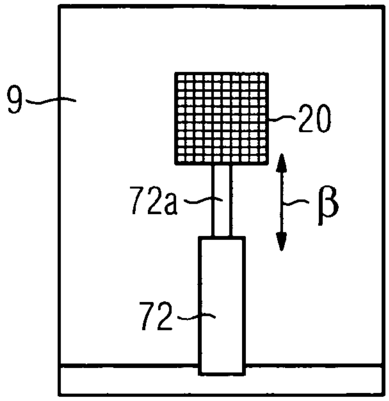

To move the second flat panel detector 20 along the arrow β, the holding section 72 comprises a holding element 72*a* which can be moved along the arrow β, as shown in FIG. 8. The movement of the holding element 72*a* in respect of the arrow β is controlled by the computer 11 of the C-arm X-ray device.

To move the second flat panel detector 20 in respect of the arrow δ, the holding section 72 is arranged on a further holding section 73 which in turn is supported on the first flat panel detector 9 such that it can be tilted, as shown in FIG.

Figure 9:
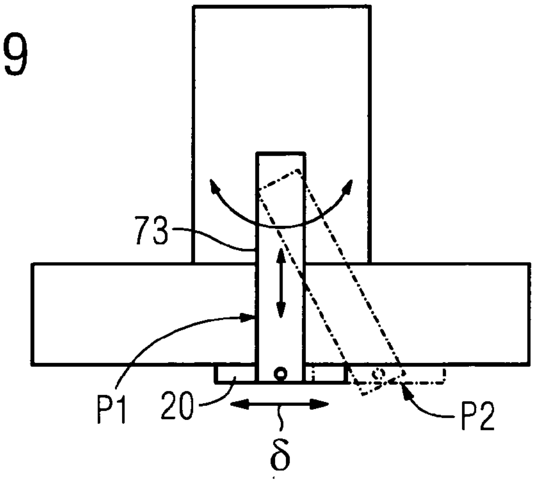

9. In FIG. 9 the holding section 72 is shown in a first position P1 and in a second position 72 by means of a dashed line for purposes of illustration.

Figure 10:
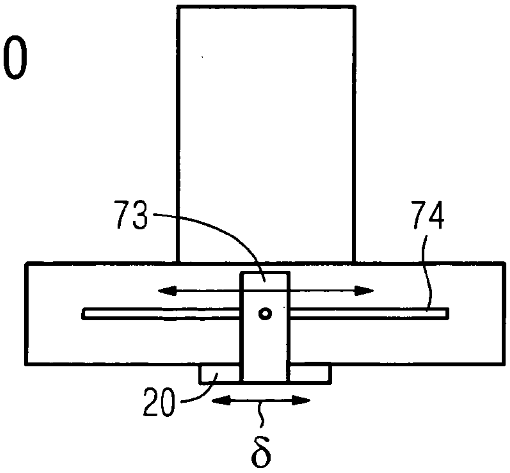
Figure 11:
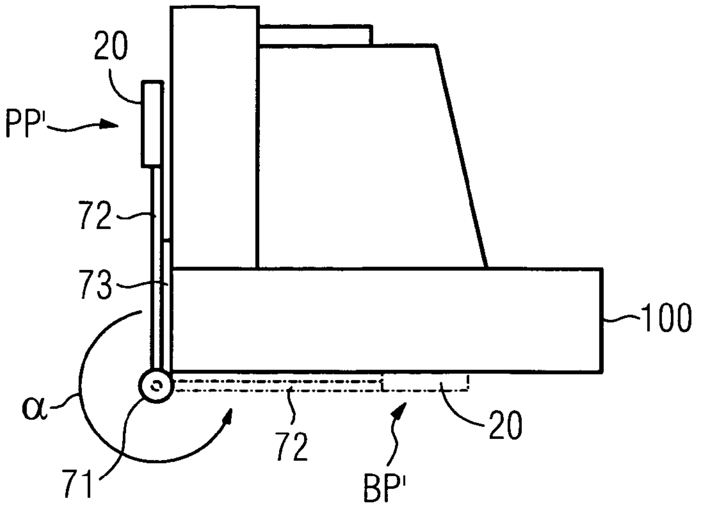
Figure 12:
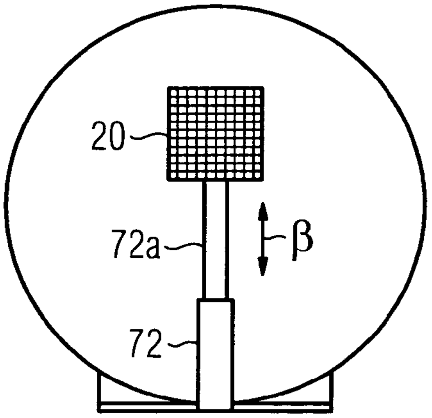
Figure 13:
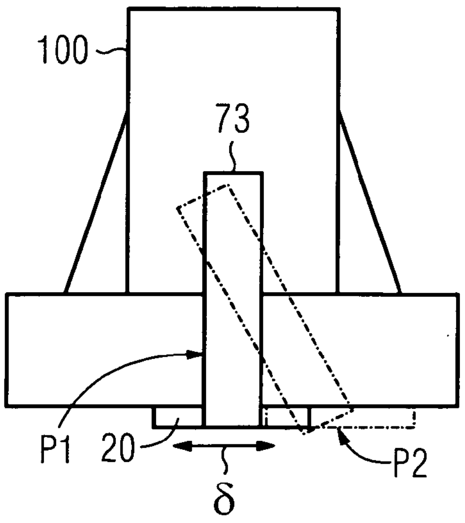

Instead of the tilting mechanism described, the holding section 73 can also be moved along a guide 74, along the arrow δ, as shown in FIG. 10.

Instead of the first flat panel detector 9, the C-arm X-ray device can also be equipped with an X-ray image amplifier 100 with a detector surface 101, as shown in FIGS. 10 to 13

The invention claimed is:

1. An X-ray device, comprising:

an X-ray source;

a first stand alone X-ray detector for generating a first X-ray image data set of an object under examination; and a second stand alone X-ray detector independent of the first stand alone X-ray detector for generating a second X-ray image data set of the object under examination, the second stand alone X-ray detector having a smaller detecting surface than the first stand alone X-ray detector and configured to acquire the second X-ray image data set with a higher local image resolution relative to the first X-ray image data set so that a second X-ray image generated from the second X-ray image data set shows a section of a first X-ray image generated from the first X-ray image data set, the section displayed in the second image having a higher image resolution than the same section displayed in the first image.

2. The X-ray device according to claim 1, wherein the second stand alone X-ray detector is a flat panel detector.

3. The X-ray device according to claim 2, wherein the flat panel detector has detecting elements having an edge length taken from the range between 20 μm and 80 μm.

4. The X-ray device according to claim 1, wherein an area of the detecting surface of the second stand alone X-ray detector is taken from the range between 15 $cm^2$ and 100 $cm^2$.

5. The X-ray device according to claim 1, wherein the second stand alone X-ray detector is arranged upstream of the first stand alone X-ray detector relative to a radiation direction from the X-ray source to the first and second stand alone X-ray detectors.

6. The X-ray device according to claim 1, further comprising an X-ray dose controlling unit for commonly controlling an X-ray dose detected by the first and second stand alone X-ray detectors.

7. The X-ray device according to claim 1, further comprising:

a display device for displaying the first X-ray image;

a selecting device for selecting the section of the first X-ray image displayed on the display device; and a positioning device for positioning the second stand alone X-ray detector so that the second X-ray image includes the section.

8. The X-ray device according to claim 7, wherein the display device and the selecting device are formed by a touch screen.

9. The X-ray device according to claim 7, wherein the selecting device includes a cursor.

10. An X-ray device comprising:

an X-ray source;

a first X-ray detector for generating a first X-ray image data set of an object under examination;

a second X-ray detector for generating a second X-ray image data set of the object under examination, the second X-ray detector having a smaller detecting surface than the first X-ray detector and configured to acquire the second X-ray image data set with a higher local image resolution relative to the first X-ray image data set so that a second X-ray image generated from the second X-ray image data set shows a section of a first X-ray image generated from the first X-ray image data set, the section displayed in the second image having a higher image resolution than the same section displayed in the first image; and a mechanical support device for accommodating the second X-ray detector.

11. A method of generating X-ray images based on X-ray image data sets using an X-ray device having an X-ray source and first and second X-ray detectors, the method comprising:

acquiring a first X-ray image data set of an object under examination by the first X-ray detector;

displaying a first X-ray image generated from the first X-ray image data set on a display device;

selecting a section of the first X-ray image;

determining image coordinates of the section relative to the first X-ray image;

aligning the second X-ray detector upstream of the first X-ray detector relative to a radiation direction from the X-ray source to the first and second X-ray detectors based on the determined image coordinates so that the second X-ray detector acquires a second X-ray image data set of the section, wherein a second X-ray image generated from the second X-ray image data set has a higher local image resolution than the first X-ray image relative to the section.

12. The method according to claim 11, wherein the display device is a touch screen, and the section is selected by touching the touch screen.

13. The method according to claim 11, wherein the section is selected using a cursor of the display device.

14. The method according to claim 11, wherein the second X-ray detector has a smaller detecting surface than the first X-ray detector.

15. The method according to claim 14, wherein the detecting surface of the second X-ray detector is taken from the range between 15 $cm^2$ and 100 $cm^2$.

16. The method according to claim 11, wherein the second X-ray detector is a flat panel detector.

17. The method according to claim 16, wherein the second X-ray detector has detector elements having an edge length taken from the range between 20 μm and 80 μm.

18. The method according to claim 11, wherein the first and second image data sets are processed by a common image processing device.

19. The method according to claim 11, wherein an X-ray dose of the first and second X-ray detectors is controlled by a common X-ray dose control unit.

* * * * *